United States Patent [19]
Alsop

[11] 3,975,775
[45] Aug. 24, 1976

[54] EXAMINING GLOVE
[76] Inventor: Reese Fell Alsop, Lloyd Lane, Lloyd Neck, Huntington, N.Y. 11743
[22] Filed: July 9, 1973
[21] Appl. No.: 377,491

[52] U.S. Cl. .................... 2/163; 2/167; 2/168; 128/262; 128/172
[51] Int. Cl.² ........................... A41D 19/00
[58] Field of Search ........... 2/159, 161 R, 167, 168, 2/163, 16, 21; 128/260, 262, 79, 132 R, 172, 2 R, 157

[56] References Cited
UNITED STATES PATENTS
3,387,307   6/1968   Blatz ........................ 2/167

FOREIGN PATENTS OR APPLICATIONS
540,241   10/1941   United Kingdom .............. 120/262

Primary Examiner—G. V. Larkin
Attorney, Agent, or Firm—Nolte and Nolte

[57] ABSTRACT

An examining glove at least one finger of which is inverted and has a rupturable seal to form a lubricant containing space. The arrangement is such so that when the glove is put on the seal is ruptured and the exterior of the glove finger is lubricated.

4 Claims, 4 Drawing Figures

EXAMINING GLOVE

BACKGROUND OF THE INVENTION

This invention is concerned with examining gloves and particularly it is concerned with providing a glove of which at least one finger is pre-lubricated.

Conventionally, when it is required to use a lubricant with examining gloves, the glove is donned and the lubricant applied to one or more of the fingers of the glove thereafter.

BRIEF SUMMARY OF THE INVENTION

According to this invention there is provided an examining glove having a lubricant containing enclosure which is ruptured when the glove is put on so that at least one of the fingers of the glove is lubricated.

More specifically, according to this invention, there is provided a glove having a plurality of fingers, one of which is at least partially everted and a rupturable seal forming a lubricant containing space within the everted portion of the finger, the length of said one finger, including the everted portion thereof, and measured from the crotch between said one finger and an adjacent finger being substantially equal to a nominal finger length for which the glove is intended, said seal being constituted, in the everted condition of said one finger, as means preventing the egress of lubricant from said lubricant containing space and, upon donning the glove, as means permitting the passage of a finger of a wearer to cause said one finger to adopt a noneverted attitude whereby the exterior surface of said one finger is lubricated.

BRIEF DESCRIPTION OF THE FIGURES OF THE DRAWINGS

Embodiments of the invention are illustrated in accompanying drawings in which.

DESCRIPTION OF THE PREFERRED EMBODIMENTS OF THE INVENTION

Figure 1:
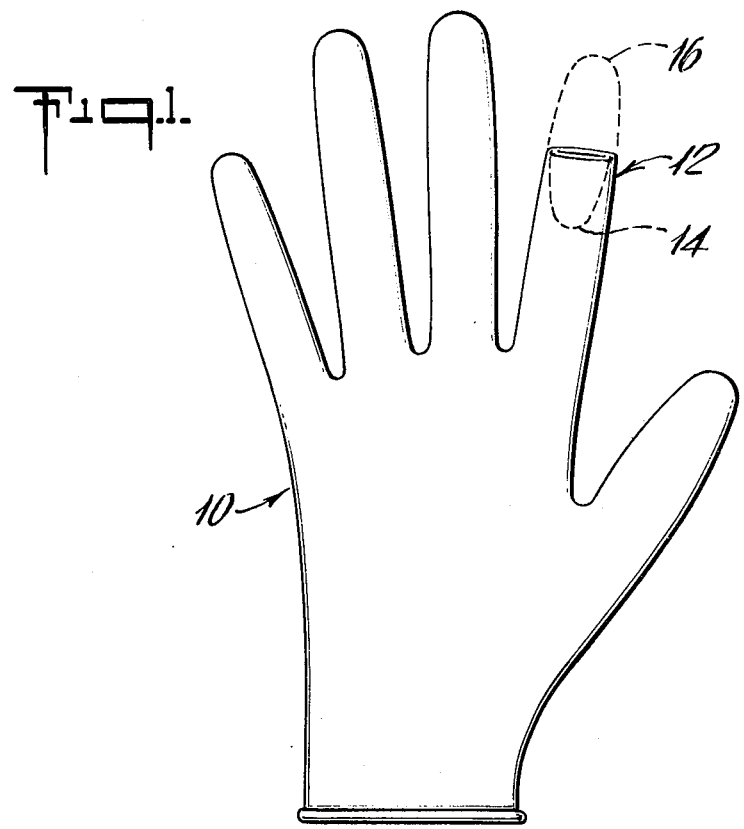
FIG. 1 is a full view of the glove.

The glove 10 in FIG. 1 is conventional except that the finger 12 has an inverted portion 14 (i.e. a portion which is turned inside out) which forms a lubricant containing enclosure as described with more detail with reference to the subsequent figures. As the glove is put on the portion 14 assumes the position shown by chain dot line 16 and the lubricant in the inverted portion 14 is of course on the outer surface of the finger 12.

Figure 2:
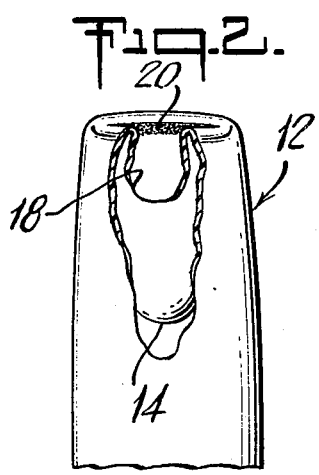
FIG. 2 is an enlarged, partially cut-away view of a part of the glove of FIG. 1.
Figure 3:
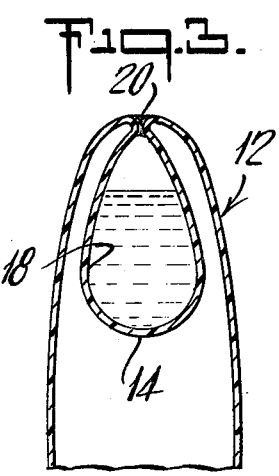
FIG. 3 is a section on the line 3—3 of FIG. 2.

Referring particularly to FIGS. 2 and 3, it will be seen that the tip portion of finger 12 is inverted to provide a lubricant containing enclosure 18 and the marginal edges of the finger while the portion 14 is inverted, are sealed by an adhesive as at 20, the seal being one which is easily ruptured as the glove is put on.

Figure 4:
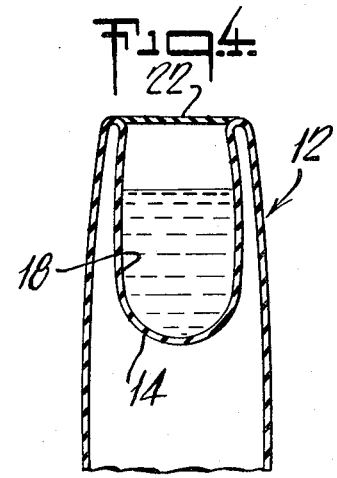
FIG. 4 is a section similar to that of FIG. 3, but of an alternate embodiment of the invention.

An alternate form of the invention is illustrated in FIG. 4 in which instead of the adhesive 20 in the embodiment of FIGS. 2 and 3 there is a rupturable membrane 22 which seals the lubricant enclosure 18.

It will be appreciated of course that the adhesive of the embodiment in FIGS. 2 and 3 is one which is selected to be compatible with the use to which the glove is put. The gloves are, as is conventional, rubber or a plastic material.

It is also to be appreciated that the lengths of the fingers of the glove, as clearly shown in the drawings, are such that when the glove is donned, the fingers conform to the fingers of the wearer to be used, as described hereabove, as a conventional examining glove, but one, of course which differs from the existing gloves in that in the very process of donning the glove, the finger to be inserted into a bodily orifice is lubricated.

What is claimed is:

1. A glove having a plurality of fingers one of which is at least partially everted and a rupturable seal forming a lubricant containing space within the everted portion of the finger, the length of said one finger including the everted portion thereof and measured from the crotch between said one finger and an adjacent finger being substantially equal to a nominal finger length for which the glove is intended, said seal being constituted, in the everted condition of said one finger, as means preventing the egress of lubricant from said lubricant containing space and, upon donning the glove, as means permitting the passage of a finger of a wearer to cause said one finger to adopt a non-everted attitude whereby the exterior surface of said one finger is lubricated.

2. A glove as claimed in claim 1 in which said seal comprises an adhesive.

3. A glove as claimed in claim 1 in which said seal comprises a membrane extending across an opening to the interior of said inverted portion of said finger.

4. A glove comprising palm and finger portions, a tip of one of said finger portions being everted, the length of said one finger portion, including said everted tip, and measured from a crotch between said one finger portion and an adjacent finger portion being substantially equal to a nominal finger length for which the glove is intended, the distal end of said one finger portion, in the everted condition, having rupturable seal means which completes a lubricant containing space defined by a surface of said tip which, when the glove is donned, becomes an exterior surface of said finger portion.

* * * * *